United States Patent
Tsujimura et al.

(10) Patent No.: US 9,884,717 B2
(45) Date of Patent: Feb. 6, 2018

(54) PACKAGE STRUCTURE FOR AGENT FOR EXTERNAL APPLICATION AND METHOD OF FABRICATING PACKAGE STRUCTURE FOR AGENT FOR EXTERNAL APPLICATION

(75) Inventors: Yasushi Tsujimura, Kanonji (JP); Daisuke Yasuki, Kanonji (JP)

(73) Assignee: KANAE TECHNOS CO., LTD., Kanonji-shi (JP)

( * ) Notice: Subject to any disclaimer, the term of this patent is extended or adjusted under 35 U.S.C. 154(b) by 282 days.

(21) Appl. No.: 13/818,352

(22) PCT Filed: Dec. 1, 2011

(86) PCT No.: PCT/JP2011/077770
§ 371 (c)(1),
(2), (4) Date: Feb. 22, 2013

(87) PCT Pub. No.: WO2012/077563
PCT Pub. Date: Jun. 14, 2012

(65) Prior Publication Data
US 2013/0146497 A1  Jun. 13, 2013

(30) Foreign Application Priority Data
Dec. 8, 2010 (JP) ................... 2010-273800

(51) Int. Cl.
*B65D 69/00* (2006.01)
*B65D 85/00* (2006.01)
(Continued)

(52) U.S. Cl.
CPC ........... *B65D 85/70* (2013.01); *A45D 44/002* (2013.01); *A61F 13/00076* (2013.01);
(Continued)

(58) Field of Classification Search
USPC ................................................. 206/581, 823
See application file for complete search history.

(56) References Cited

U.S. PATENT DOCUMENTS 2,430,459 A * 11/1947 Farrell et al. ................. 383/116
3,642,126 A *  2/1972 Kurtz ............... A61B 17/06114
                                                        206/484
(Continued)

FOREIGN PATENT DOCUMENTS

CH           618392 A5    7/1980
JP       2000-287751 A   10/2000
(Continued)

*Primary Examiner* — Jacob K Ackun
(74) *Attorney, Agent, or Firm* — Metrolexis Law Group, PLLC

(57) ABSTRACT

[Purpose] The disclosure provides a package structure of an agent for skin external application, which is unfolded upon the opening of the package structure and very easily separated from the stack structure, and a method of fabricating the package structure for the agent for skin external application.

[Constitution] An agent 2 for skin external application is interposed between a film-type base material 3 and a film-type cover material 4, the resultant product is folded by employing the cover material 4 as a folding surface, and the four-layer overlap material including the base material 3-the cover material 4-the cover material 4-the base material 3 provided at a peripheral portion of the folded structure is closed through thermal bonding.

9 Claims, 10 Drawing Sheets

(51) Int. Cl.
   A45D 44/00      (2006.01)
   A61F 13/00      (2006.01)
   A61F 13/02      (2006.01)
   B65D 75/20      (2006.01)
   B65D 75/30      (2006.01)
   B31B 50/26      (2017.01)

(52) U.S. Cl.
   CPC .......... *A61F 13/0276* (2013.01); *B31B 50/26* (2017.08); *B65D 75/20* (2013.01); *B65D 75/30* (2013.01); *A45D 2200/1027* (2013.01); *A45D 2200/1036* (2013.01); *A61F 2013/00646* (2013.01); *A61F 2013/0296* (2013.01)

(56) References Cited

U.S. PATENT DOCUMENTS

| | | | | |
|---|---|---|---|---|
| 4,196,809 | A * | 4/1980 | Tonrey | B65D 77/2064 206/459.5 |
| 4,696,393 | A * | 9/1987 | Laipply | 206/210 |
| 4,915,102 | A * | 4/1990 | Kwiatek | A61F 13/023 206/440 |
| 6,059,112 | A * | 5/2000 | Dykstra | A61B 19/026 206/438 |
| 6,139,188 | A * | 10/2000 | Marzano | 383/110 |
| 6,170,653 | B1 * | 1/2001 | Panzner | B65D 81/3261 206/205 |
| 6,280,085 | B1 * | 8/2001 | Beer | B31B 37/00 206/484 |
| 6,402,727 | B1 * | 6/2002 | Rosengrant | 604/385.02 |
| 6,530,477 | B1 * | 3/2003 | Martorano et al. | 206/524.2 |
| 7,204,368 | B2 * | 4/2007 | Cheaure | B65D 31/12 206/440 |
| 7,631,766 | B2 * | 12/2009 | Wang | 206/581 |
| 2005/0147328 | A1 | 7/2005 | Cheaure et al. | |

FOREIGN PATENT DOCUMENTS

| | | |
|---|---|---|
| JP | 2005-112441 A | 4/2005 |
| JP | 2006-224974 A | 8/2006 |
| JP | 2008-266191 A | 11/2008 |
| JP | 2009-113856 A | 5/2009 |

* cited by examiner

PACKAGE STRUCTURE FOR AGENT FOR EXTERNAL APPLICATION AND METHOD OF FABRICATING PACKAGE STRUCTURE FOR AGENT FOR EXTERNAL APPLICATION

TECHNICAL FIELD

The present invention relates to a package structure for an agent for skin external application. A packaged agent for skin external application adhering to a skin surface in use and a method of fabricating the package structure for the agent for skin external applications are provided.

BACKGROUND ART

In general, agents for skin external application adhering to a skin surface in use are mainly classified into an agent including an adhesive surface formed by coating a medical fluid with viscosity on one surface of a film-type or a sheet-type support and an agent prepared by infiltrating a medical fluid into a film-type or a sheet-type support. The above agents are individually packaged to prevent the adhesive surfaces from being contaminated or dried when they are supplied for distribution and preservation.

Among such agents for skin external application, a relatively large-size agent for skin external application that adheres to a facial surface of a user in use, is generally folded in a predetermined size and individually packaged in a packaging material (see patent document 1).

CITED REFERENCES

Patent Documents

Patent Document 1: Japanese Unexamined Patent Publication No. 2000-287751

DISCLOSURE OF THE INVENTION

Technical Problem

When using the folded agent for skin external application packaged in the packaging material, the agent for skin external application must be separated from the packaging material. The agent for skin external application, which has been separated from the packaging materials, must be unfolded.

However, since the agent for skin external application has the form of a thin film or a thin sheet, the agent for skin external application may be torn or deformed by the stress occurring when the agent for skin external application is separated from the packaging material. Since agents for skin external application adhering to the face of a user in use have the facial shape of a human, many agents for skin external application are formed therein with openings or notches. Accordingly, when the agents for skin external application are separated from the packaging material, the opening or the notch may often tear. In addition, a work for unfolding the folded agent for skin external application is very complicated. Also, the agent for skin external application may be torn when the agent for skin external application is unfolded.

The present invention has been made by taking the above problems into consideration. The present invention provides a package structure for an agent for skin external application, which can be unfolded upon the opening of the package structure and very readily separated from the package structure, and a method of fabricating the package structure for the agent for skin external application.

Means for Solving the Problem

A package structure for an agent for skin external application, according to the present invention, is used for packaging a film-type agent or a sheet-type agent for skin external application adhering to a skin surface in use. The package structure for the agent for skin external application includes a skin adhesive agent interposed between a film-type or sheet-type base material and a film-type or sheet-type cover material. The package structure is folded while employing the cover material as a folding surface. Also, a four-layer overlap material including the base material-the cover material-the cover material-the base material provided at a peripheral portion of the package structure, is closed through thermal bonding (hereinafter, this structure will be referred to as the package structure of the present invention).

According to the package structure of the present invention, preferably, the seal strength between the cover material-the cover material is greater than the seal strength between the base material-the cover material in the four-layer overlap material, is closed through the thermal bonding.

In addition, preferably, a material constituting the base material is different from a material constituting the cover material.

Further, preferably, the base material is a metal-deposited film, or a metal-deposited sheet, and the cover material is a polymer film or a polymer sheet.

According to a method of fabricating a package structure for an agent for skin external application of the present invention, a stack structure is formed by interposing a film-type or sheet-type agent for skin external application between a film-type or sheet-type base material and a film-type or sheet-type cover material. Positions of the base material and the cover material are determined by thermally bonding a portion of a two-layer overlap material including the base material-the cover material provided at a peripheral portion of the stack structure. The stack structure is folded while employing the cover material as a folding surface. An overlap material, including the base material-the cover material-the cover material-the base material provided at a peripheral portion of the folded stack structure, is closed through thermal bonding.

Effect of the Invention

According to the present invention, the agent for skin external application can be unfolded upon the opening of the package structure so that the agent can be very readily separated from the package structure.

EMBODIMENTS FOR CARRYING OUT THE INVENTION

Hereinafter, embodiments of the present invention will be described with reference to the accompanying drawings. In addition, the present invention is not limited to the embodiments.

Embodiment 1

Figure 1A:
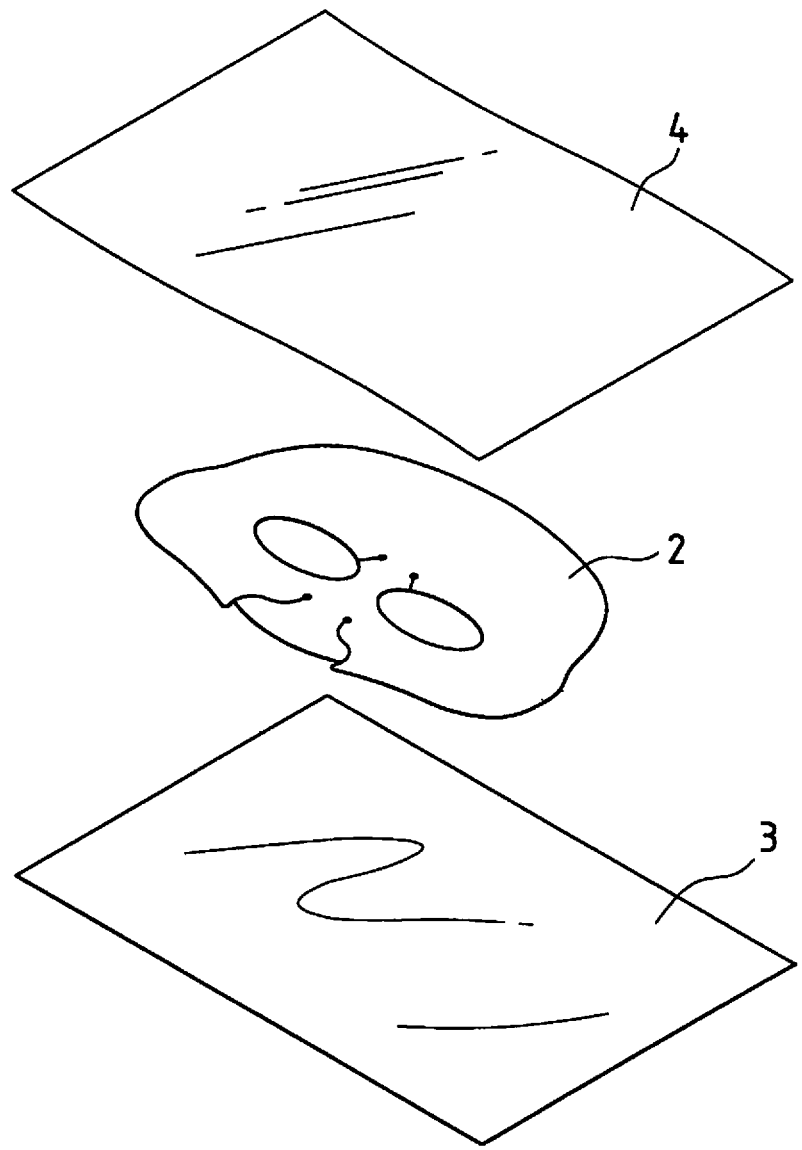
FIGS. 1A and 1B are a perspective view and a sectional view showing a cladding process in the fabrication process of a package structure, according to the first embodiment of the present invention, respectively.
Figure 1B:
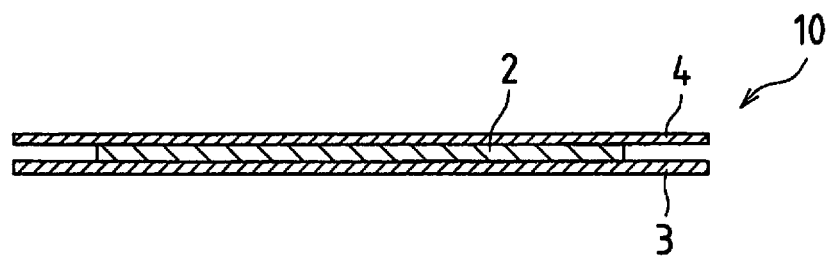

According to the first embodiment, as shown in FIG. 1A, a cladding process of forming a stack structure 10 including a base material 3-an agent 2 for skin external application-a cover material 4 shown in FIG. 1B is performed by interposing the sheet-type agent 2 for skin external application between surfaces of the film-type base material 3 and the film-type cover material 4, which are overlapped with each other.

The present invention may not specially limit the size, the shape, and bonding positions of the agent 2 for skin external application if the agent 2 adhering to a skin surface in use can allow pharmaceutical ingredients to be absorbed into a body through a skin or the agent 2 provides one of glossiness, moisturizing, and a feeling of refreshment to the skin. In addition, the present invention may not specially limit the attribute of the agent 2 for skin external application, but the agent 2 for skin external application may include cosmetics, medicines, medical supplies, or miscellaneous goods. The agent 2 for skin external application is mainly classified into an agent prepared by infiltrating a liquid medicine into a film-type support or a sheet-type support and an agent prepared by coating a liquid medicine having viscosity on one surface of the film-type support or the sheet-type support. Any one of the above agents is applicable to a package structure 1 of the present invention. The present invention may not specially limit the support if the support has flexibility and predetermined shape retention. In general, preferably, the support may include non-woven fabric, woven fabric, paper, a plastic film, or a hydro-gel having the shape retention.

According to the present embodiment, the agent 2 for skin external application is prepared by infiltrating a liquid medicine (cosmetic liquid) into a hydro-gel serving as a support. The agent 2 for skin external application has a shape to cover the upper face of a human, and has openings corresponding to the eyes of the human and a notch formed in a portion corresponding to the nose of the human.

The base material 3 and the cover material 4 have surface sizes (face sizes) large enough to have an extra portion after covering the agent 2 for skin external application. In other words, the base material 3 and the cover material 4 have sizes greater than the surface size of the agent 2 for skin external application. Accordingly, in the stack structure 10, the peripheral portions of the base material 3 and the cover material 4 are separated from the circumference of the agent 2 for skin external application and left as surplus portions that form a two-layer overlap material including the base material 3-the cover material 4. Although the base material 3 and the cover material 4 generally have the same shape to be overlapped in match with each other, the base material 3 and the cover material 4 may have different shapes if the base material 3 and the cover material 4 have surfaces sizes large enough to have the extra portion after covering the agent 2 for skin external application.

The base material 3 and the cover material 4 may be prepared by using various flexible films or sheets having non-air permeability without special limitation. In general, the base material 3 and the cover material 4 may include polymer films or polymer sheets. They are processed in the form of films or sheets by using one or at least two selected from polymer materials such as polyethylene, polypropylene, polyester, polyamide, polyimide, polycarbonate, ethylene-vinyl acetate copolymer, ethylene-ethyl acrylate copolymer polypropylene-ethylene random copolymer and polyvinyl chloride, or metal-deposited films or metal-deposited sheets. These polymer materials are prepared by depositing metal such as aluminum (Al) on one side or both sides of a polymer film or a polymer sheet. The polymer films or the polymer sheets which are a multiple-layer structure formed by stacking a plurality of polymer films or a plurality of polymer sheets, may be used. In addition, although the base material 3 and the cover material 4 may be formed by using the same material, the base material 3 and the cover material 4 may be preferably formed by using materials different from each other.

According to the embodiment, the base material 3 is formed using a metal-deposited film prepared by depositing metal (aluminum (Al)) on one side of a polymer film made of polypropylene, and the cover material 4 is formed by using a polymer film prepared by processing polypropylene-ethylene random copolymer in the form of a film. The metal-deposited film used for the base material 3 has a superior air barrier property and high film strength. Meanwhile, the polymer film including a polypropylene-ethylene random co polymer and used for the cover material 4, has superior transparency and has a property that may control the seal strength in thermal bonding, according to the content of ethylene, as a co-monomer. According to the embodiment, the agent 2 for skin external application is interposed between the base material 3 and the cover material 4 such that the metal-deposited surface of the base material 3 faces the cover material 4.

However, in general, ⌈film(type)⌋ refers to a film having a thickness of less than 0.2 mm, and ⌈sheet(type)⌋ refers to a sheet having a thickness of 0.2 mm or more. According to the present invention, the agent 2 for skin external application, the base material 3, and the cover material 4 may employ the film type or the sheet type.

Figure 2:
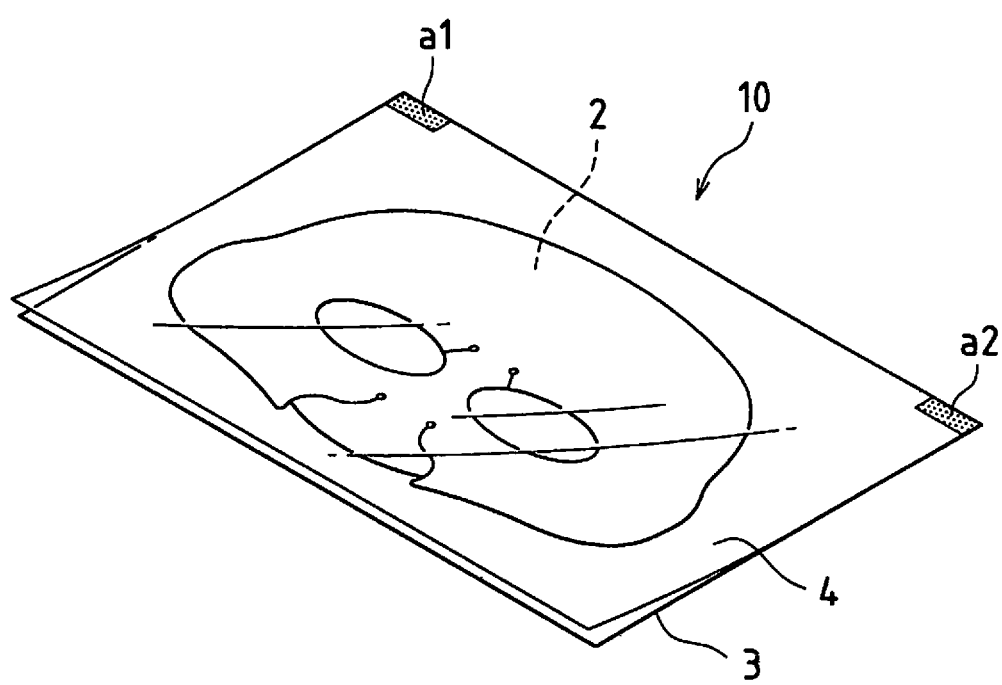
FIG. 2 is a perspective view showing a positioning process in the fabrication process of the package structure, according to the first embodiment, of the present invention.

According to the present embodiment, as shown in FIG. 2, after the cladding process has been performed, a process of determining the positions of the base material 3 and the cover material 4 is performed by thermally bonding portions of the two-layer overlap material including the base material 3-the cover material 4, which are provided at the peripheral portions of the stack structure 10. The thermal bonding positions in the positioning process are not specially limited. According to the present embodiment, the positions of the base material 3 and the cover material 4 are determined by thermally bonding two corner portions a1 and a2.

In addition, in the subsequent process, in the case that the base material 3 cannot be misaligned with the cover material 4, or the base material 3 and the cover material 4 are slightly misaligned within the allowable range. The positioning process may be omitted.

Figure 3A:
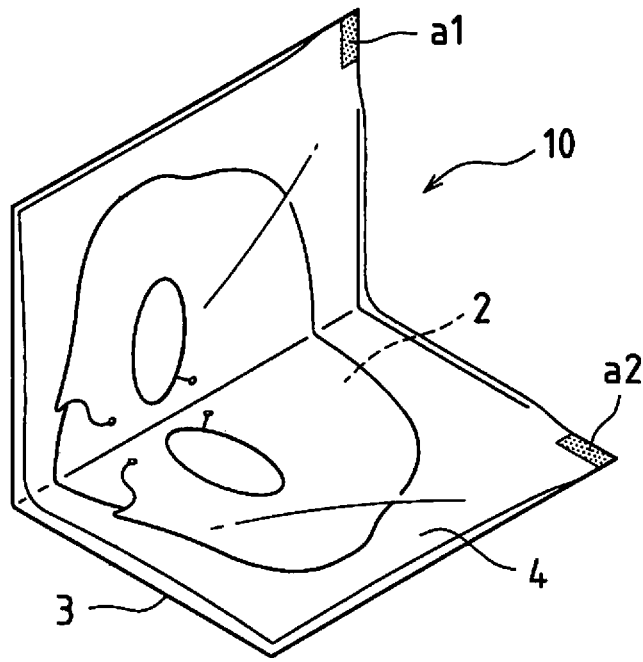
FIGS. 3A and 3B are a perspective view and a sectional view showing a folding process in the fabrication process of the package structure, according to the first embodiment of the present invention, respectively.

According to the present embodiment, as shown in FIG. 3A, after the positioning process has been performed, a process of folding the stack structure 10 is performed while employing the cover material 4 as a folding surface. Since the positions of the base material 3 and the cover material 4 have been determined through the positioning process, the base material 3 is not misaligned with the cover material 3 when the folding process is performed.

Figure 3B:
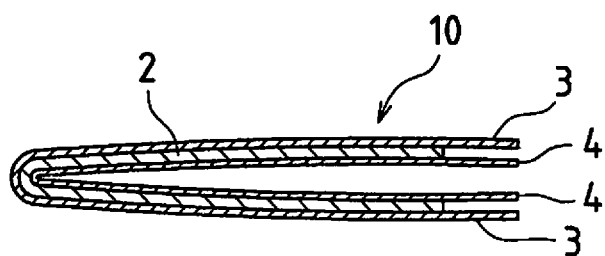

In addition, since the two-layer overlap material including the base material 3-the cover material 4 are partially thermal-bonded to each other through the thermal bonding performed in the positioning process, the extra air between the base material 3 and the cover material 4 is rapidly discharged from the gap between non-thermally bonded portions of the two-layer overlap material including the base material 3-the cover material 4 when the folding process is performed. Accordingly, the stack structure 10 can be easily folded without the extra air between the base material 3 and the cover material 4. Due to the folding process, the four-layer overlap material including the base material 3-the cover material 4-the cover material 4-the base material 3 are provided at the peripheral portion of the folded stack structure 10 (see FIG. 3B).

Figure 4:
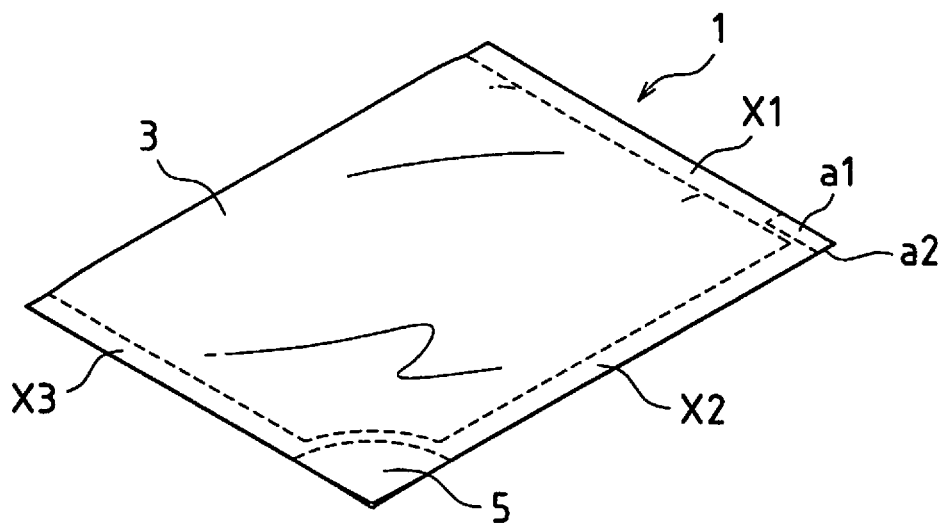
FIG. 4 is a perspective view showing the package structure according to the first embodiment of the present invention.

According to the embodiment, after the folding process has been performed, a seal process of closing the four-layer overlap material including the base material 3-the cover material 4-the cover material 4-the base material 3, which are provided at the peripheral portions of the stack structure 10, is performed through thermal bonding. According to the present embodiment, the four-layer overlap material is closed by thermally bonding outer peripheral portions X1 to X3 except for the folding line of the stack structure 10 (see FIG. 4). In addition, according to the present embodiment, a grip part 5 that is not subject to the thermal bonding must be provided at one corner portion of the stack structure 10, and related portions to be thermally bonded are provided inside the stack structure 10.

The thermal bonding between the cover material 4-the cover material 4 disposed at the inner portion of the four-layer overlap material thermally bonded in the seal process is performed by thermally bonding homogenous polymer films with each other. Meanwhile, the thermal bonding between the base material 3-the cover material 4 at both outer portions of the four-layer overlap material is performed by thermally bonding the heterogeneous materials of the polymer film and the metal-deposited film. In general, the seal strength resulting from the thermal bonding between the homogenous materials is greater than the seal strength resulting from the thermal bonding between the heterogeneous materials. According to the present embodiment, the seal strength resulting from the thermal bonding between the cover material 4-the cover material 4, that is, between the homogeneous polymer films becomes greater than the seal strength between the base material 3-the cover material 4, that is, between the heterogeneous materials of the polymer film and the metal-deposited film.

After the above processes have been finished, the package structure 1, according to the first embodiment of the present invention, is fabricated. The package structure 1, according to the present invention, may be individually packaged or a plurality of package structures 1, which are packaged once more, may be packaged and then supplied for distribution or preservation. Since the base material 3, including the metal-deposited film having high strength, serves as the outermost layer, the package structure 1, according to the present invention, represents high strength against the physical stress caused by the friction or the bending applied to the package structure 1 when the package structure 1 is distributed or preserved. In addition, since the agent 2 for skin external application contained in the package structure 1, according to the present invention, is supported in the state that the agent 2 is fitted into the folding portions of the package structure 1, according to the present invention, the agent 2 for skin external application is rarely biased when the package structure 1 is distributed or preserved.

Figure 5A:
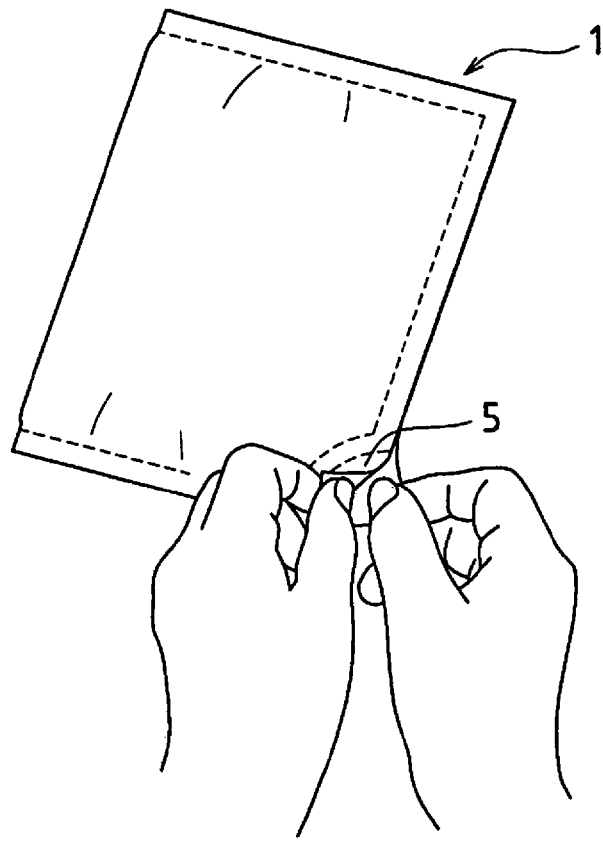
FIGS. 5A and 5B are perspective views showing the state that the package structure according to the first embodiment of the present invention is being open.

When opening the package structure 1, according to the present invention to separate the contained agent 2 for skin external application from the package structure 1, a user grips the grip part 5 with fingers and unfolds the package structure 1, according to the present invention, while delaminating the portions of the package structure 1 closed through the thermal bonding as shown in FIG. 5A. While unfolding the package structure 1, according to the present invention, the contained agent 2 for skin external application is unfolded. Accordingly, an additional work is not required to unfold the folded agent 2 for skin external application. In addition, according to the present embodiment, since the cover material 4 includes a transparent material, the user can recognize the agent 2 for skin external application, which is unfolded while the package structure 1, according to the present invention, is unfolded with the naked eyes.

Figure 5B:
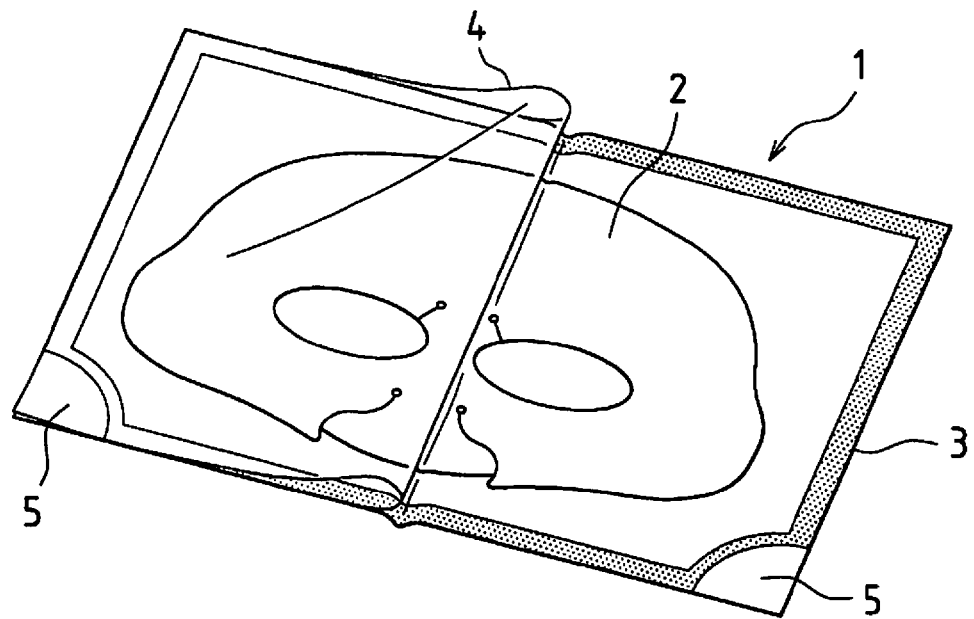

In particular, according to the present embodiment, the seal strength resulting from the thermal bonding between the homogeneous materials of the cover material 4-the cover material 4 becomes greater than the seal strength between the heterogeneous materials of the base material 3-the cover material 4. When the package structure 1, according to the present invention, is open, the thermally bonded portions of the base material 3-the cover material 4 is primarily unsealed. In other words, as shown in FIG. 5B, when unfolding the package structure 1 according to the present invention, the thermally bonded portions between the base material 2-the cover material 4 are delaminated from each other at one side (the right side of the drawing) of the package structure 1, according to the present invention about a folding line of the package structure 1. At the other side of the package structure 1, since the thermally bonded portions between the cover material 4-the cover material 4 are rarely delaminated from each other, only the cover material 4 is moved to the other side (the right side in the drawing) of the package structure 1 while maintaining the folding state. In other words, since the cover material 4 is delaminated up to the folding line when the package structure 1 according to the present invention is unfolded, the subsequent work for removing the cover material 4 can be more easily performed.

After unfolding the package structure 1, according to the present invention, the remaining thermally bonded portions between the base material 3 and the cover material 4 are delaminated from each other and the cover material 4 is removed. In this case, the agent 2 for skin external application is exposed in the unfolding state on the base material 3.

When the agent 2 for skin external application exposed in the unfolding state on the base material 3 adheres to the facial surface of the user, it is possible to adhere the agent 2 for skin external application to the facial surface of the user after separating the agent 2 for skin external application from the base material 3, or the base material 3 may be removed after the agent 2 for skin external application has individually adhered to the facial surface of the user. Even if either of the above cases is employed, the agent 2 for skin external application may easily separate, from the package structure 1 according to the present invention or may easily adhere to the facial surface, so that the agent 2 for skin external application is not torn.

The package structure 1 prepared, according to the first embodiment of the present invention, is folded two times in such a manner that the cover material 4 serves as a folding surface. However, only if the package structure 1 is folded in such a manner that the cover material 4 serves as the folding surface. The number of times to fold the package structure 1 is not limited to two times. For example, the package structure 1 may be folded through a folding scheme named "gate fold", or "z-fold". Hereinafter, the gate-folded package structure 1 according to the second embodiment of the present invention will be described Embodiment 2

According to the second embodiment, similarly to the first embodiment (see FIGS. 1A and 1B), a cladding process of forming the stack structure 10 including the base material 3-the agent 2 for skin external application-the cover material 4 is performed by interposing the agent 2 for skin external application between surfaces of the film-type base material 3 and the film-type cover material 4, which are overlapping each other.

Figure 6:
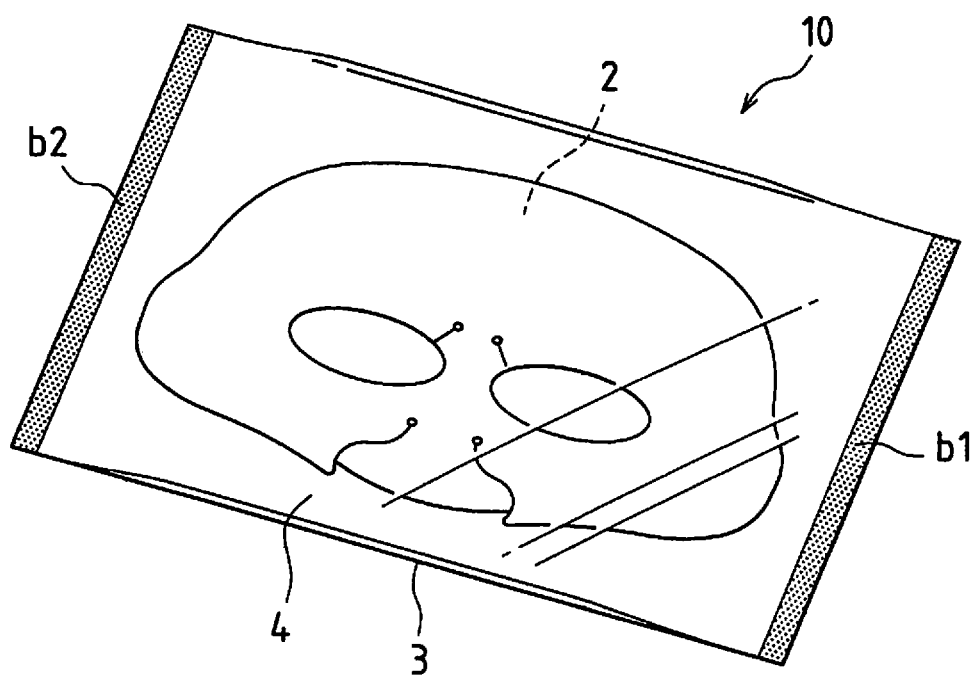
FIG. 6 is a perspective view showing a positioning process in the fabrication process of the package structure according to the second embodiment of the present invention.

According to the present embodiment, as shown in FIG. 6, after the cladding process has been performed, a positioning process of determining the positions of the base material 3 and the cover material 4 is performed by thermally bonding both opposite edge portions b1 and b2 (both edges portions at the right and left sides of the drawing) of the stack structure 10.

Figure 7:
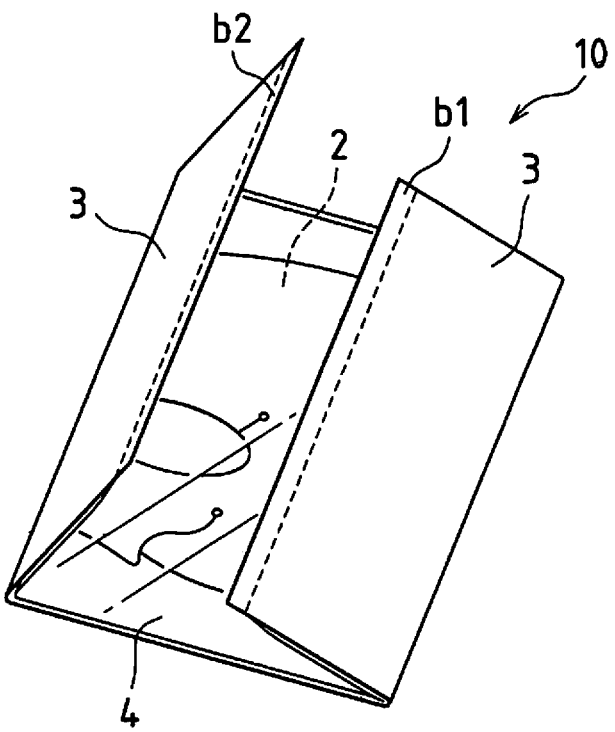
FIG. 7 is a perspective view showing a folding process in the fabrication process of the package structure, according to the second embodiment of the present invention.

According to the present embodiment, as shown in FIG. 7, after the positioning process has been performed, a folding process of gate-folding the stack structure 10, while employing the cover material 4 as a folding surface, is performed.

Figure 8:
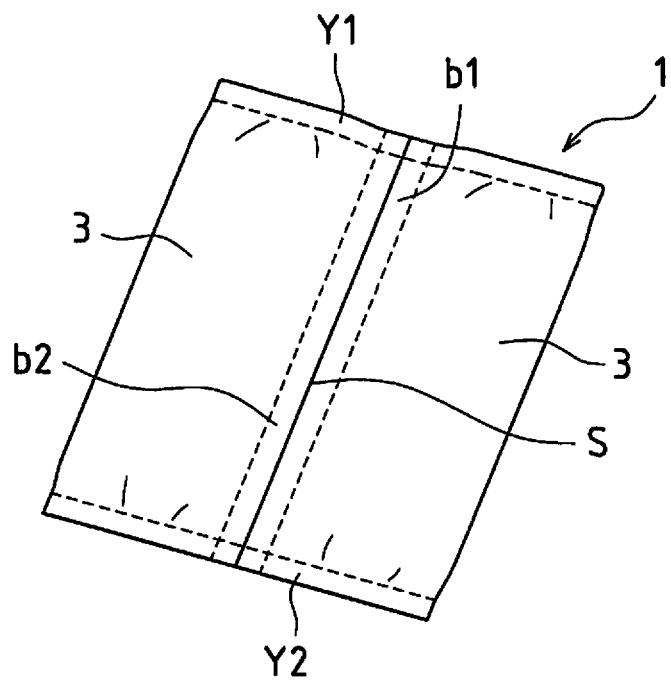
FIG. 8 is a perspective view showing the package structure, according to the second embodiment, of the present invention.

According to the present embodiment, after the folding process has been performed, a seal process of closing the four-layer overlap material including the base material 3-the cover material 4-the cover material 4-the base material 3, which are provided at the peripheral portions of the folded stack structure 10, is performed through thermal bonding. According to the present embodiment, the four-layer overlap material are closed by thermally bonding outer peripheral portions Y1 and Y2 except for the folding line of the stack structure 10 (see FIG. 8).

Figure 9:
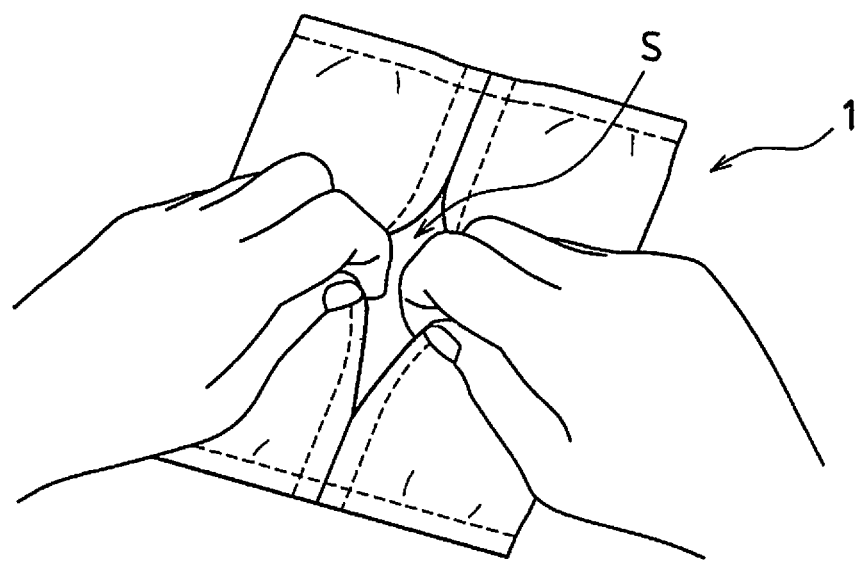
FIG. 9 is a perspective view showing the state that the package structure, according to the second embodiment of the present invention, is being open.

After the above processes have been finished, the package structure 1, according to the second embodiment of the present invention, is fabricated. When opening the package structure 1, according to the present invention to separate the contained agent 2 for skin external application from the package structure 1, a user inserts fingers into a slit S formed through the gate fold of the package structure 1 as shown in FIG. 9 to open the package structure 1 in bi-lateral directions and delaminating the thermally bonded portions of the package structure 1. Thereby, while unfolding package structure 1, the package spreads out the agent 2 for skin external application, according to the present invention.

Since the remaining components are substantially the same as the components according to the first embodiment, the details thereof will be omitted in order to avoid redundancy.

Although the package structure 1 according to the first and second embodiments is formed by packaging the relatively large-size agent 2 adhering to the facial surface of the user in use, the package structure 1 according to the present invention can also package the smaller agent 2 for skin external application. Hereinafter, the package structure 1 according to the present invention that packages two smaller agents 2 for skin external application according to the third embodiment, which adhere to the skin below the eyes of the user in use, will be described.

Embodiment 3

Figure 10:
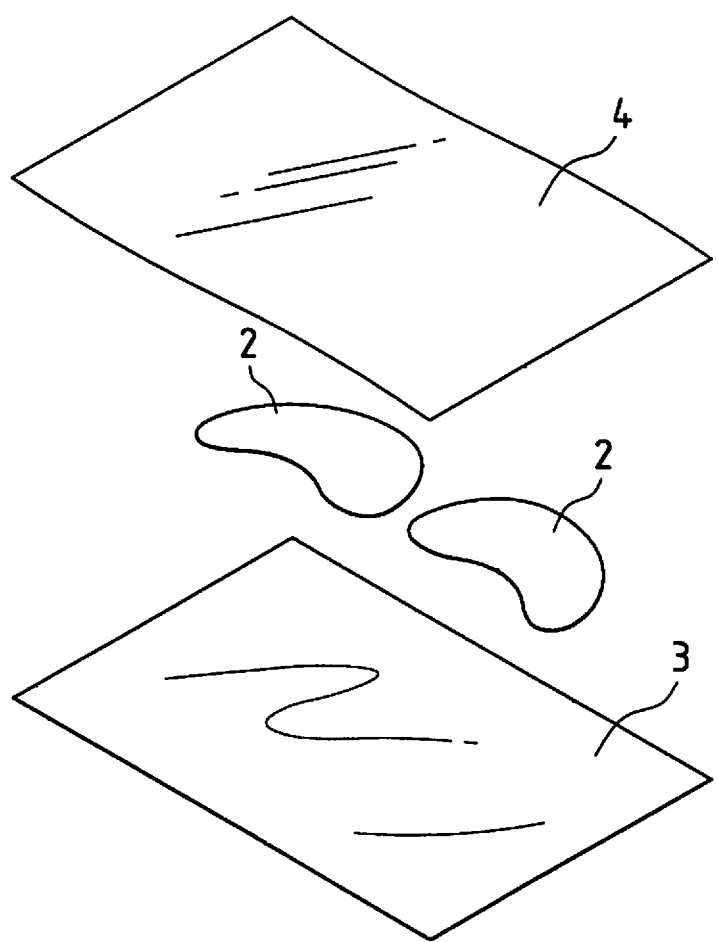
FIG. 10 is a perspective view showing a cladding process in the fabrication process of a package structure, according to the third embodiment of the present invention.

According to the third embodiment, as shown in FIG. 10, the two smaller agents 2 for skin external application are placed on the film-type base material 3 in the state that the two smaller agents 2 for skin external application are arranged. Two smaller agents 2 for skin external application are interposed between the base material 3 and the cover material 4 by covering the two smaller agents 2 for skin external application by the film-type cover material 4, thereby completing a cladding process of forming the stack structure 10.

Figure 11:
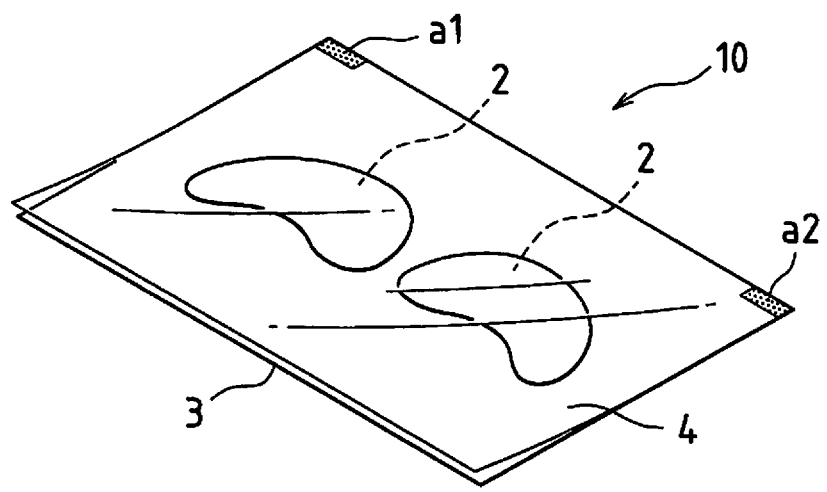
FIG. 11 is a perspective view showing a positioning process in the fabrication process of the package structure, according to the third embodiment, of the present invention.

According to the present embodiment, as shown in FIG. 11, after the cladding process has been performed, a positioning process of determining the positions of the base material 3 and the cover material 4 is performed by thermally bonding two corner portions a1 and a2 of the stack structure 10.

Figure 12:
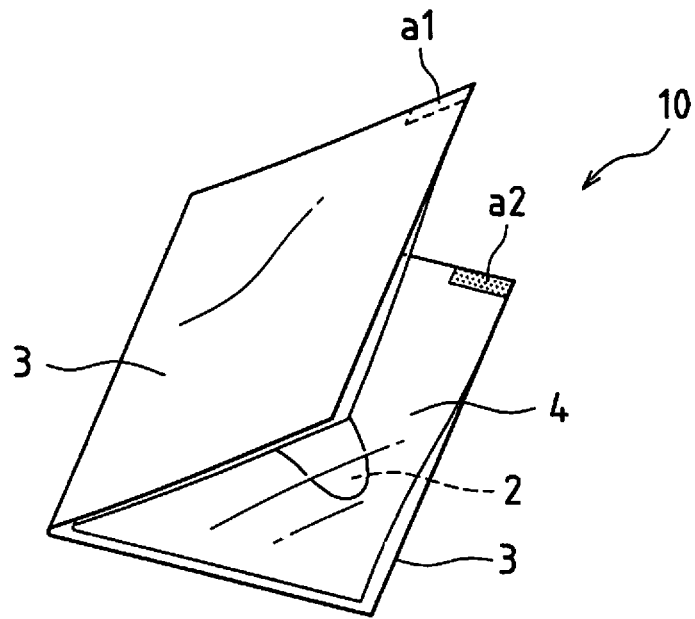
FIG. 12 is a perspective view showing a folding process in the fabrication process of the package structure, according to the third embodiment, of the present invention.

According to the present embodiment, as shown in FIG. 12, after the positioning process has been performed, a folding process of folding the stack structure 10 is performed while employing the cover material 4 as a folding surface. In this case, the two smaller agents 2 for skin external application are arranged about the folding line of the folded stack structure 10.

Figure 13:
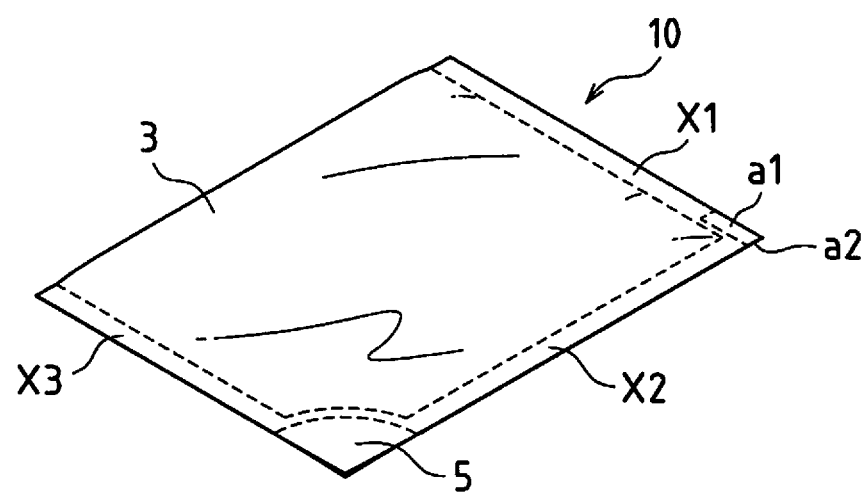
FIG. 13 is a perspective view showing the package structure, according to the third embodiment, of the present invention.

According to the present embodiment, after the folding process has been performed, a seal process of closing the four-layer overlap material, including the base material 3-the cover material 4-the cover material 4-the base material 3, which are provided at the peripheral portions of the folded stack structure 10, is performed through thermal bonding. Similarly to the first embodiment, according to the present embodiment, the four-layer overlap material are closed by thermally bonding outer peripheral portions X1 to X2 except for the folding line of the stack structure 10 (see FIG. 13).

Figure 14:
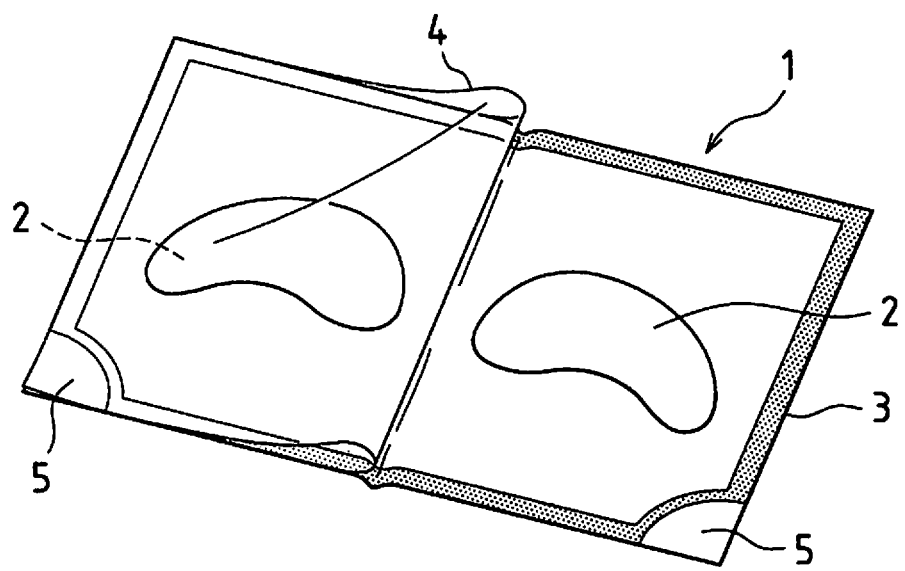
FIG. 14 is a perspective view showing the state that the package structure according to the third embodiment of the present invention has been open.

After the above processes have been finished, the package structure 1, according to the third embodiment of the present invention, is fabricated. When opening the package structure 1, according to the present invention to separate the contained agents 2 for skin external application from the package structure 1, a user grips the grip part 5 with the fingers thereof and unfolds the package structure 1, according to the present invention, while delaminating the thermally closed portions, similarly to the first embodiment (see FIG. 5A). If the package structure 1, according to the present invention is unfolded, the two agents for skin external application are arranged at both sides about the folding line of the package structure 1, according to the present invention, as shown in FIG. 14.

Since the remaining components are substantially the same as the components according to the first embodiment, the details thereof will be omitted in order to avoid redundancy.

INDUSTRIAL APPLICABILITY

The package structure according to the present invention and the method of fabricating the same are suitable for agents for skin external application, which are distributed as cosmetics, medicines, medical supplies, or miscellaneous goods.

DESCRIPTION OF REFERENCE NUMERALS

1: package structure of present invention
2: agent for skin external application
3: base material
4: cover material
5: grip part
10: stack structure

The invention claimed is:

1. A package comprising a skin external application agent and having a sheet shape,
   wherein the package comprises a folded stack structure that includes a base material, the skin external application agent, and a cover material in a state in which the base material, the skin external application agent, and the cover material are folded about a folding line with the skin external application agent being interposed between the base material and the cover material such that the folded stack structure comprises a six layer structure of base material layer, skin external application agent, cover material layer, cover material layer, skin external application agent, and base material layer in vicinity of the folding line of the folded stack structure,
   wherein the folded stack structure comprises a four layer structure of base material layer, cover material layer, cover material layer and base material layer at peripheral portion of the folded stack structure except for the folding line,
   wherein the peripheral portion of the four layer structure, except for the folding line, is sealed by thermal bonding,
   wherein the folded stack structure comprises a grip part at one corner portion of the peripheral portion, the grip part at the one corner portion being away from the folded line, and
   wherein the grip part at the one corner portion is not subject to being sealed by thermal bonding.

2. The package of claim 1, wherein the base material is different from the cover material.

3. The package of claim 1, wherein the base material is a metal-deposited film of less than 0.2 mm thickness, or a metal-deposited sheet of thickness 0.2 mm or more, and the cover material is a polymer film of less than 0.2 mm thickness or a polymer sheet of thickness 0.2 mm or more.

4. The package of claim 1, wherein the base material consists of aluminum deposited film on one side of a polypropylene polymer.

5. The package of claim 4, wherein the cover material consists of a film of polypropylene-ethylene random copolymer.

6. The package of claim 1, wherein the skin external application agent is a hydrogel that contains cosmetic liquid.

7. The package of claim 1, wherein the peripheral portion of the four layer structure is sealed with a thermal bond between polymer film of the cover material layer and metal deposited film of the base material layer.

8. The package of claim 7, wherein the cover material consists of a film of polypropylene-ethylene random copolymer.

9. The package of claim 1, wherein the cover material is transparent.

* * * * *